(12) United States Patent
Crawford et al.

(10) Patent No.: US 8,424,541 B2
(45) Date of Patent: Apr. 23, 2013

(54) TOBACCO-FREE ORAL FLAVOR DELIVERY POUCH PRODUCT

(75) Inventors: Danielle R. Crawford, Chester, VA (US); Karen Brooks, Midlothian, VA (US); Kenneth A. Newman, Prince George, VA (US); William R. Sweeney, Richmond, VA (US); Fernando L. Chappell, Sr., Colonial Heights, VA (US)

(73) Assignee: Philip Morris USA Inc., Richmond, VA (US)

( * ) Notice: Subject to any disclaimer, the term of this patent is extended or adjusted under 35 U.S.C. 154(b) by 388 days.

(21) Appl. No.: 12/219,118

(22) Filed: Jul. 16, 2008

(65) Prior Publication Data

US 2009/0025741 A1 Jan. 29, 2009

Related U.S. Application Data

(60) Provisional application No. 60/929,875, filed on Jul. 16, 2007.

(51) Int. Cl.
*A24B 15/00* (2006.01)
(52) U.S. Cl.
USPC .......................................... 131/352; 131/359
(58) Field of Classification Search ................. 131/352, 131/359
See application file for complete search history.

(56) References Cited

U.S. PATENT DOCUMENTS

| 307,537 A | 11/1884 | Foulks |
| 1,234,279 A | 7/1917 | Buchanan |
| 1,376,586 A | 5/1921 | Schwartz |
| 1,992,152 A | 2/1935 | Yeates |
| 2,313,696 A | 3/1941 | Yates |
| 2,306,400 A | 12/1942 | Menzel |
| 2,318,101 A | 5/1943 | Rose |
| 2,330,361 A | 9/1943 | Howard |
| 2,528,778 A | 11/1950 | Piazze |
| 3,067,068 A * | 12/1962 | Finberg ..................... 131/359 |
| 3,162,199 A | 12/1964 | Moll, Jr. |
| 3,174,889 A | 3/1965 | Anderson et al. |

(Continued)

FOREIGN PATENT DOCUMENTS

| EP | 0212234 A2 | 7/1986 | |
| EP | 0 245 575 | * 11/1987 | ..................... 426/77 |

(Continued)

OTHER PUBLICATIONS

Dixit, R.P. et al, "Oral Strip Technology: Overview and future potential", Journal of Controlled Release, Jun. 24, 2009, pp. 94-107.*

(Continued)

*Primary Examiner* — Richard Crispino
*Assistant Examiner* — Dionne Walls Mayes
(74) *Attorney, Agent, or Firm* — Buchanan Ingersoll & Rooney PC

(57) ABSTRACT

Provided is a tobacco-free oral flavor delivery pouch product that provides and engaging and flavorful experience to a user. The pouch product includes a porous pouch wrapper and an inner filling material. The inner filling material can include a non-tobacco, botanical component, at least one functional ingredient and a solid flavor component dispersed throughout the inner filling material. The pouch product delivers multiple textures to the user's mouth.

19 Claims, 2 Drawing Sheets

U.S. PATENT DOCUMENTS

| | | | |
|---|---|---|---|
| 3,188,265 A | 6/1965 | Charbonneau et al. | |
| 3,369,551 A | 2/1968 | Carroll | |
| 3,415,286 A | 12/1968 | Arnold et al. | |
| 3,600,807 A | 8/1971 | Sipos | |
| 3,607,299 A | 9/1971 | Bolt | |
| 3,692,536 A | 9/1972 | Fant | |
| 3,757,798 A | 9/1973 | Lambert | |
| 3,846,569 A | 11/1974 | Kaplan | |
| 3,932,192 A | 1/1976 | Nakashio et al. | |
| 4,218,286 A | 8/1980 | Jones et al. | |
| 4,347,857 A | 9/1982 | Boden | |
| 4,386,106 A | 5/1983 | Merritt et al. | |
| 4,515,769 A | 5/1985 | Merritt et al. | |
| 4,545,392 A | 10/1985 | Sensabaugh et al. | |
| 4,565,702 A | 1/1986 | Morley et al. | |
| 4,607,479 A | 8/1986 | Linden | |
| 4,624,269 A | 11/1986 | Story et al. | |
| 4,660,577 A | 4/1987 | Sensabaugh et al. | |
| 4,703,765 A | 11/1987 | Paules et al. | |
| 4,797,287 A | 1/1989 | Pich et al. | |
| 4,880,697 A | 11/1989 | Caldwell et al. | |
| 4,892,483 A | 1/1990 | Douglas, Jr. | |
| 4,893,639 A | 1/1990 | White | |
| 4,906,488 A | 3/1990 | Pera | |
| 4,907,605 A | 3/1990 | Ray et al. | |
| 4,917,161 A | 4/1990 | Townend | |
| 4,971,797 A | 11/1990 | Cherukuri et al. | |
| 4,981,522 A | 1/1991 | Nichols et al. | |
| 5,127,208 A | 7/1992 | Custer et al. | |
| 5,144,964 A | 9/1992 | Demain | |
| 5,167,244 A | 12/1992 | Kjerstad | |
| 5,174,088 A | 12/1992 | Focke et al. | |
| 5,186,185 A | 2/1993 | Mashiko et al. | |
| 5,211,985 A | 5/1993 | Shirley, Jr. et al. | |
| 5,240,016 A | 8/1993 | Nichols et al. | |
| 5,263,999 A | 11/1993 | Baldwin et al. | |
| 5,346,734 A | 9/1994 | Wydick, Jr. | |
| 5,372,149 A | 12/1994 | Roth et al. | |
| 5,387,416 A | 2/1995 | White et al. | |
| 5,479,949 A | 1/1996 | Battard et al. | |
| 5,525,351 A | 6/1996 | Dam | |
| 5,549,906 A | 8/1996 | Santus | |
| 5,601,716 A | 2/1997 | Heinrich et al. | |
| 5,726,161 A | 3/1998 | Whistler | |
| 5,733,559 A | 3/1998 | Citernesi | |
| 5,773,062 A | 6/1998 | Cirigliano et al. | |
| 5,780,055 A | 7/1998 | Habib et al. | |
| 5,806,408 A | 9/1998 | DeBacker et al. | |
| 5,829,453 A | 11/1998 | White et al. | |
| 5,921,955 A | 7/1999 | Mazer et al. | |
| 5,927,052 A | 7/1999 | Nippes et al. | |
| 5,997,691 A | 12/1999 | Gautam et al. | |
| 6,046,177 A | 4/2000 | Stella et al. | |
| 6,048,736 A | 4/2000 | Kosak | |
| 6,135,120 A | 10/2000 | Löfman et al. | |
| 6,143,316 A | 11/2000 | Hayden et al. | |
| 6,146,655 A | 11/2000 | Ruben | |
| 6,162,516 A | 12/2000 | Derr | |
| 6,280,761 B1 | 8/2001 | Santus | |
| 6,287,603 B1 | 9/2001 | Prasad et al. | |
| 6,287,612 B1 | 9/2001 | Mandava et al. | |
| 6,325,859 B1 | 12/2001 | De Roos et al. | |
| 6,383,475 B1 | 5/2002 | Meyers et al. | |
| 6,414,033 B1 | 7/2002 | Sceusa | |
| 6,444,253 B1 | 9/2002 | Conklin et al. | |
| 6,455,068 B1 | 9/2002 | Licari | |
| 6,557,561 B1 | 5/2003 | Miyauchi et al. | |
| 6,565,710 B2 | 5/2003 | Salow et al. | |
| 6,706,120 B2 | 3/2004 | Miyauchi et al. | |
| D489,606 S | 5/2004 | Lofman | |
| 6,793,949 B2 | 9/2004 | Panesar | |
| 6,871,473 B1 | 3/2005 | Dutt et al. | |
| 6,878,695 B2 | 4/2005 | Woo et al. | |
| 6,884,885 B2 | 4/2005 | Qi | |
| 6,895,974 B2 | 5/2005 | Peele | |
| 6,942,848 B2 | 9/2005 | Nelson et al. | |
| 6,958,429 B2 | 10/2005 | Bruhn et al. | |
| 6,982,093 B2 | 1/2006 | Licari | |
| 6,984,376 B2 | 1/2006 | Stephenson et al. | |
| 7,030,092 B1 | 4/2006 | Levine | |
| 7,032,601 B2 | 4/2006 | Atchley et al. | |
| 7,090,858 B2 | 8/2006 | Jayaraman | |
| 7,115,586 B2 | 10/2006 | Loftsson | |
| 7,166,671 B2 | 1/2007 | Wood et al. | |
| 7,186,701 B2 | 3/2007 | Kubota et al. | |
| RE40,059 E * | 2/2008 | Pacifico et al. | 427/213.3 |
| D568,576 S | 5/2008 | Neidle et al. | |
| D585,626 S | 2/2009 | Chappell, Sr. et al. | |
| 7,584,843 B2 | 9/2009 | Kutsch et al. | |
| 2002/0012689 A1 | 1/2002 | Stillman | |
| 2002/0170567 A1* | 11/2002 | Rizzotto et al. | 131/359 |
| 2003/0070687 A1 | 4/2003 | Atchley et al. | |
| 2003/0109492 A1 | 6/2003 | Loftsson | |
| 2003/0224090 A1 | 12/2003 | Pearce et al. | |
| 2004/0015756 A1 | 1/2004 | Chiu | |
| 2004/0018293 A1* | 1/2004 | Popplewell et al. | 426/650 |
| 2004/0037879 A1 | 2/2004 | Adusumilli et al. | |
| 2004/0118421 A1 | 6/2004 | Hodin et al. | |
| 2004/0123873 A1 | 7/2004 | Calandro et al. | |
| 2004/0129280 A1 | 7/2004 | Woodson et al. | |
| 2004/0145261 A1 | 7/2004 | Ganter et al. | |
| 2004/0191322 A1 | 9/2004 | Hansson | |
| 2004/0191366 A1 | 9/2004 | Mangos et al. | |
| 2004/0202698 A1 | 10/2004 | Ramji et al. | |
| 2004/0234479 A1 | 11/2004 | Schleifenbaum et al. | |
| 2004/0247649 A1 | 12/2004 | Pearce et al. | |
| 2004/0247744 A1 | 12/2004 | Pearce et al. | |
| 2004/0247746 A1 | 12/2004 | Pearce et al. | |
| 2005/0000531 A1 | 1/2005 | Shi | |
| 2005/0003048 A1 | 1/2005 | Pearce et al. | |
| 2005/0034738 A1 | 2/2005 | Whalen | |
| 2005/0061339 A1 | 3/2005 | Hansson et al. | |
| 2005/0081264 A1 | 4/2005 | Brugliera et al. | |
| 2005/0100640 A1 | 5/2005 | Pearce | |
| 2005/0172976 A1 | 8/2005 | Newman et al. | |
| 2005/0178398 A1 | 8/2005 | Breslin et al. | |
| 2005/0210615 A1 | 9/2005 | Shastry et al. | |
| 2005/0241656 A1 | 11/2005 | Kennison | |
| 2005/0244521 A1 | 11/2005 | Strickland et al. | |
| 2005/0287249 A1 | 12/2005 | Shukla et al. | |
| 2006/0039973 A1 | 2/2006 | Aldritt et al. | |
| 2006/0073190 A1 | 4/2006 | Carroll et al. | |
| 2006/0118589 A1 | 6/2006 | Arnarp et al. | |
| 2006/0144412 A1 | 7/2006 | Mishra et al. | |
| 2006/0174901 A1 | 8/2006 | Karles et al. | |
| 2006/0191548 A1* | 8/2006 | Strickland et al. | 131/347 |
| 2006/0204598 A1 | 9/2006 | Thompson | |
| 2006/0228431 A1* | 10/2006 | Eben et al. | 424/729 |
| 2006/0231113 A1 | 10/2006 | Newbery et al. | |
| 2006/0272662 A1 | 12/2006 | Jupe et al. | |
| 2006/0275344 A1 | 12/2006 | Mody et al. | |
| 2007/0000505 A1 | 1/2007 | Zhuang et al. | |
| 2007/0012328 A1* | 1/2007 | Winterson et al. | 131/347 |
| 2007/0048431 A1 | 3/2007 | Budwig et al. | |
| 2007/0062549 A1 | 3/2007 | Holton, Jr. et al. | |
| 2007/0077307 A1 | 4/2007 | Rosenberg et al. | |
| 2007/0095356 A1 | 5/2007 | Winterson et al. | |
| 2007/0107747 A1 | 5/2007 | Hill et al. | |
| 2007/0122526 A1 | 5/2007 | Sweeney et al. | |
| 2007/0186941 A1 | 8/2007 | Holton, Jr. et al. | |
| 2007/0186942 A1 | 8/2007 | Strickland et al. | |
| 2007/0186943 A1 | 8/2007 | Strickland et al. | |
| 2007/0186944 A1 | 8/2007 | Strickland et al. | |
| 2007/0190157 A1 | 8/2007 | Sanghvi et al. | |
| 2007/0207239 A1 | 9/2007 | Neidle et al. | |
| 2007/0261707 A1 | 11/2007 | Winterson et al. | |
| 2007/0267033 A1 | 11/2007 | Mishra et al. | |
| 2007/0298061 A1 | 12/2007 | Boghani et al. | |
| 2008/0014303 A1 | 1/2008 | Jacops et al. | |
| 2008/0029110 A1 | 2/2008 | Dube et al. | |
| 2008/0029116 A1 | 2/2008 | Robinson et al. | |
| 2008/0029117 A1 | 2/2008 | Mua et al. | |
| 2008/0081071 A1 | 4/2008 | Sanghvi et al. | |
| 2008/0113031 A1 | 5/2008 | Moodley et al. | |
| 2008/0166395 A1 | 7/2008 | Roush | |
| 2008/0173317 A1 | 7/2008 | Robinson et al. | |
| 2008/0196730 A1 | 8/2008 | Engstrom et al. | |

| | | | |
|---|---|---|---|
| 2008/0202536 A1 | 8/2008 | Torrence et al. | |
| 2008/0302682 A1 | 12/2008 | Engstrom et al. | |
| 2008/0308115 A1 | 12/2008 | Zimmerman et al. | |
| 2008/0317911 A1 | 12/2008 | Schleef et al. | |
| 2009/0004329 A1 | 1/2009 | Gedevanishvili et al. | |
| 2009/0022856 A1 | 1/2009 | Cheng et al. | |
| 2009/0022917 A1 | 1/2009 | Gedevanishvili et al. | |
| 2009/0025740 A1 | 1/2009 | Chappell, Sr. et al. | |
| 2009/0035414 A1 | 2/2009 | Cheng et al. | |
| 2009/0126746 A1 | 5/2009 | Strickland et al. | |
| 2010/0218779 A1 | 9/2010 | Zhuang et al. | |
| 2010/0300464 A1 | 12/2010 | Gee et al. | |
| 2010/0300465 A1 | 12/2010 | Zimmerman | |

FOREIGN PATENT DOCUMENTS

| | | |
|---|---|---|
| EP | 0 145 499 | 4/1989 |
| EP | 0352107 A2 | 1/1990 |
| EP | 0483500 A1 | 5/1992 |
| EP | 0 422 898 | 9/1994 |
| EP | 0 599 425 | 10/1997 |
| EP | 1010639 A1 | 6/2000 |
| EP | 1118274 A | 7/2001 |
| GB | 725764 | 3/1955 |
| GB | 924052 | 4/1963 |
| GB | 1139684 | 1/1969 |
| GB | 1350740 | 4/1974 |
| GB | 2074838 A | 11/1981 |
| JP | 03-240665 | 10/1991 |
| WO | WO 94/25356 | 11/1994 |
| WO | WO 97/45336 | 12/1997 |
| WO | WO 99/40799 | 8/1999 |
| WO | WO 00/57713 * | 10/2000 |
| WO | WO 01/70591 A1 | 9/2001 |
| WO | WO 02/080707 A1 | 10/2002 |
| WO | WO 03/028492 A1 | 4/2003 |
| WO | WO 03/030881 | 4/2003 |
| WO | WO 03/053175 A2 | 7/2003 |
| WO | WO 2004/009445 | 1/2004 |
| WO | WO 2004/052335 | 6/2004 |
| WO | WO 2004/056219 | 7/2004 |
| WO | WO 2004/058217 | 7/2004 |
| WO | WO 2004/064811 A1 | 8/2004 |
| WO | WO 2004/066986 | 8/2004 |
| WO | WO 2004/095959 A1 | 11/2004 |
| WO | WO 2005/027815 | 3/2005 |
| WO | WO 2005/046363 | 5/2005 |
| WO | WO 2005/077232 | 8/2005 |
| WO | WO 2005/084446 | 9/2005 |
| WO | WO 2006/004480 A1 | 1/2006 |
| WO | WO 2006/039487 A | 4/2006 |
| WO | WO 2006/065192 | 6/2006 |
| WO | WO2006/090290 A | 8/2006 |
| WO | WO 2006/105173 A2 | 10/2006 |
| WO | WO 2006/120570 A2 | 11/2006 |
| WO | WO 2006/127772 A | 11/2006 |
| WO | WO2007/037962 A1 | 4/2007 |
| WO | WO2007/057789 A2 | 5/2007 |
| WO | WO2007/057791 A2 | 5/2007 |
| WO | WO2007/082599 A1 | 7/2007 |
| WO | WO 2007/104573 | 9/2007 |
| WO | WO 2007/126361 A1 | 11/2007 |
| WO | WO 2008/016520 A2 | 2/2008 |
| WO | WO 2008/042331 A2 | 4/2008 |
| WO | WO 2008/104891 A2 | 9/2008 |
| WO | WO 2008/140372 A1 | 11/2008 |

OTHER PUBLICATIONS

"Benefits of Honey", Honey Nutrition Facts, http://www.benefits-of-honey.com/honey-nutrition.html, 2 pages printed from the Internet on Jan. 5, 2012.*
International Preliminary Report on Patentability issued Jan. 19, 2010 for PCT/IB2008/002764.
International Search Report and Written Opinion mailed Mar. 24, 2009 for PCT/IB2008/002764.
International Search Report and Written Opinion mailed Jul. 17, 2009 for PCT/IB2008/002714.
International Preliminary Report on Patentability issued Jan. 19, 2010 for PCT/IB2008/002714.
U.S. Appl. No. 12/789,125 to Mishra et al., filed May 27, 2010.
International Search Report and Written Opinion dated Aug. 6, 2007 for PCT/IB2006/004077.
Partial International Search Report dated Oct. 6, 2006 for PCT/IB2006/001611.
International Search Report and Written Opinion dated Feb. 27, 2007 for PCT/IB2006/002680.
International Preliminary Report on Patentability dated Oct. 30, 2007 for PCT/IB2006/001611.
International Preliminary Report on Patentability mailed Dec. 16, 2008 for PCT/IB2006/002680.
International Search Report and Written Opinion dated Sep. 12, 2008 for PCT/IB2008/001378.
International Search Report and Written Opinion dated Jan. 30, 2009 for PCT/IB2008/002598.
International Search Report and Written Opinion mailed Feb. 25, 2009 for PCT/IB2008/002566.
International Preliminary Report on Patentability issued Dec. 11, 2009 for PCT/IB2008/002598.
International Search Report and Written Opinion mailed Mar. 25, 2009 for PCT/IB2008/002682.
International Preliminary Report on Patentability issued Jan. 19, 2010 for PCT/IB2008/002682.
International Search Report and Written Opinion mailed Mar. 31, 2009 for PCT/IB2008/002681.
International Search Report and Written Opinion mailed Jul. 25, 2006 for PCT/IB2006/001114.
U.S. Appl. No. 12/805,868, filed Aug. 20, 2010.
U.S. Appl. No. 12/748,043, filed Mar. 26, 2010.
U.S. Appl. No. 12/748,205, filed Mar. 26, 2010.
U.S. Appl. No. 12/642,399, filed Dec. 18, 2009.
International Preliminary Report on Patentability dated Aug. 28, 2007 for PCT/IB2006/001114.
International Search Report and Written Opinion mailed Mar. 13, 2009 for PCT/IB2008/002694.
International Preliminary Report on Patentability issued Jan. 19, 2010 for PCT/IB2008/002694.
Satel, Sally M.D., "A Smokeless Alternative to Quitting," Apr. 6, 2004, The New York Times, Accessed Oct. 25, 2010; http://query.nytimes.com/gst/fullpage.html?res=9402EFD91E39F935A35757C0A9629C8B63.

* cited by examiner

TOBACCO-FREE ORAL FLAVOR DELIVERY POUCH PRODUCT

CROSS REFERENCE TO RELATED APPLICATION

This application claims priority under 35 U.S.C. §119(e) to U.S. provisional Application No. 60/929,875, filed on Jul. 16, 2007, the entire content of which is incorporated herein by reference.

SUMMARY

Provided is a tobacco-free oral flavor delivery pouch product for providing an engaging, functional and flavorful oral experience to a user.

In an embodiment, the tobacco-free oral flavor delivery pouch product includes a porous pouch wrapper, which encloses an inner filling material. Also preferably, the flavors and juices from the inner filling material are able to exit the pouch via the pores in the pouch wrapper. In a preferred embodiment, the inner filling material includes a non-tobacco, botanical component, at least one functional ingredient, such as a food grade functional ingredient, and a solid flavor component, such as a flavor strip and/or flavor beads. Preferably, each component of the inner filling material provides a different flavor, function, and/or texture.

In a preferred embodiment, the porous pouch wrapper is made of a fabric, paper or non-dissolvable plastics or polymers, such as those known in the art and used in the production of tea bags or oral, smokeless tobacco pouches. However, dissolvable or disintegrable polymers may be used to form the pouch wrapper. The porous pouch wrapper can be colored.

Preferably, the porous, outer pouch wrapper has encapsulated flavorants incorporated therein. Also, functional ingredients may be incorporated in the pouch wrapper via coating or embedding.

DETAILED DESCRIPTION

As described herein, an oral flavor delivery pouch product provides an engaging, flavorful, aromatic, energizing, and/or soothing experience by delivering ingredients to a user in a consumable unit. Preferably, an inner filling material is enclosed in a porous pouch wrapper that is designed to be inserted in the mouth. The inner filling material includes a non-tobacco, botanical component, at least one functional ingredient and a solid flavor component. The at least one functional ingredient can include an effervescent, a vitamin, a soothing ingredient, an energizing ingredient and/or a chemesthesis agent. In a preferred embodiment, each ingredient provides a different texture or flavor to enhance the oral enjoyment of the product.

As used herein, the term "texture" describes the feel, sensation, appearance, consistency, and/or quality of each ingredient of the pouch product.

As used herein, the term "solid flavor component" describes films, strips, bits, rods, beads, granules, capsules, microcapsules, powders, and the like that include flavorants therein.

Figure 1:
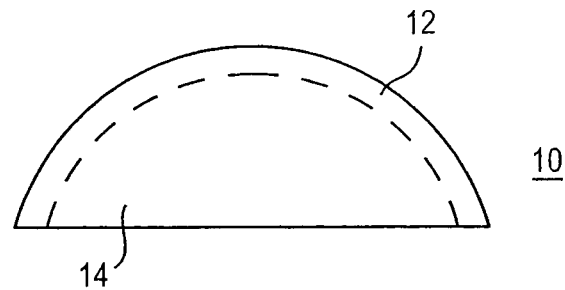
FIG. 1 is an illustration of an oral flavor delivery pouch product.

As best seen in FIG. 1, an oral flavor delivery pouch product 10 is provided. Preferably, the oral flavor delivery pouch product includes a porous, pouch wrapper 14 that has a seal 12 around edges thereof to enclose an inner filling material 16 (shown in FIG. 2).

In a preferred embodiment, the oral flavor delivery pouch product 10 provides flavor for about 1 minute to about 60 minutes. More preferably, the pouch product provides flavor for about 1 minute to 45 minutes or about 5 minutes to about 45 minutes (e.g., about 5 minutes to about 30 minutes, about 10 minutes to about 20 minutes, about 15 minutes to about 30 minutes, about 30 minutes to about 60 minutes).

Preferably, the oral flavor delivery pouch product 10 weighs about 0.2 g to about 5.0 g (e.g., about 0.1 g to about 1.0 g, about 1.0 g to about 2.0 g, about 2.0 g to about 3.0 g, about 3.0 g to about 4.0 g or about 4.0 g to about 5.0 g). Also preferably, the oral flavor delivery pouch product 10 is about 0.25 inch to about 2.0 inches in width, about 0.25 inch to about 2.0 inches in length, and about 0.25 inch to about 2.0 inches thick. In an embodiment, the oral flavor delivery pouch product 10 is about 0.1 inch to about 2.0 inches in width, about 0.1 inch to about 2.0 inches in length and about 0.1 inch to about 2.0 inches thick.

Preferably, the oral flavor delivery pouch product 10 fits completely and comfortably inside the user's mouth. Preferably, the oral flavor delivery pouch product 10 fits discreetly within the user's mouth, and more preferably between the cheek and teeth or gums. A user can suck, chew, or otherwise orally manipulate the pouch product 10 to release the flavors contained therein.

Preferred pouch shapes include round, polygonal, symmetrical, or non-symmetrical shapes such as a half moon, D-shaped, crescent, oblong, cylindrical, tea leaf, tear drop, or hourglass shapes. Other shapes may be utilized so long as the shapes are comfortable, do not have sharp edges, and fit discreetly in a user's mouth. In an embodiment, the shape of the pouch product 10 indicates the flavor and/or functional ingredients contained therein. For example, a tea leaf shaped pouch can contain teas and/or tea extracts.

Figure 4:
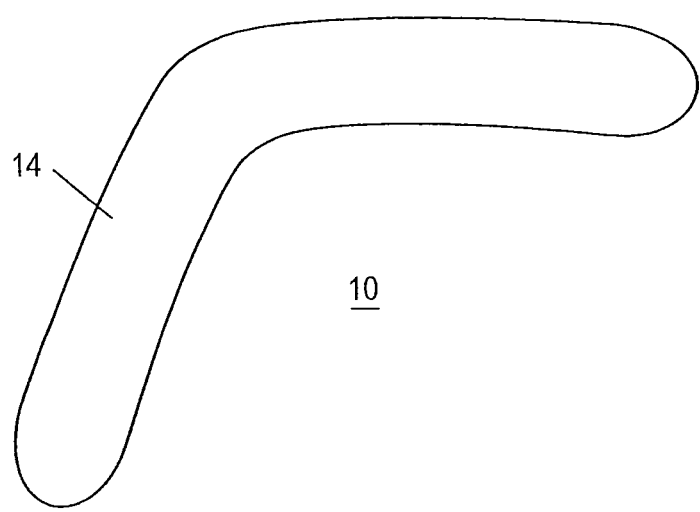
FIG. 4 is an illustration of an oral flavor delivery pouch product formed in a boomerang shape.

In an embodiment, the pouch 10 is shaped like a boomerang, as shown in FIG. 4. The boomerang shaped pouch 10 has long arms that can be more easily orally manipulated during use as compared to pouches without projections. Each arm can be up to about 2.0 inches long, more preferably up to about 1.0 inch long, and up to about 1.0 inch wide, more preferably up to about 0.5 inch wide. When placed in the mouth, between the cheek and gum, each arm can extend around the gum line, potentially covering more area within the mouth than pouches having other shapes. As such, the flavors and functional ingredients from the pouch are dispersed over a larger area of the mouth, such that the flavor is not as concentrated in one area of the mouth as compared pouches having other shapes. Also, because of the extended arms, the boomerang shaped pouch 10 has a larger surface area and greater fill capacity, which provides potentially longer lasting flavor and functionality as compared to pouches 10 having other shapes. The extended arms can also be tucked under the tongue or against the roof of the mouth through oral manipulation, which can provide a different experience as compared to pouches held between the cheek and gum.

The boomerang shaped pouch can be made on high speed vertical or horizontal filling machines. In an embodiment, the boomerang shaped pouch can be made by cutting the pouch material into a D-shape prior to filling. Once filled, the D-shape is modified to the boomerang shape by sealing and/or cutting. In another embodiment, the pouch material can be cut into a boomerang shape prior to filling and sealing. For example, the boomerang shaped pouch can be formed by cutting a sheet of material, folding the cut material end to end lengthwise and sealing the folded end with a half circle seal. Then, the material is cut at the left and right edge of the seal. The material is then opened, folded and aligned such that the width edges are in the shape of a "V." The "V" shaped material is placed in a specially made sealing block for stage two sealing. When the stage two seal is initiated the boomerang pouch seal will have an opening at the top for insertion of the filling material. Once filled the pouch material is placed on a sealing block for a final seal at the crown or opening of the boomerang. The material is then placed on the cutter, which cuts an outer line shape of the boomerang, while maintaining and providing for a soft edge pouch.

In a preferred embodiment, the pouch wrapper 14 is made of a porous, outer material. Preferably, the porous, outer material allows the flavors and functional ingredients to diffuse out of the pouch wrapper 14 and into the user's mouth. A preferred wrapper 14 is a permeable polymer material such as a non-woven synthetic polymer. The wrapper 14 can be a spunbond polymer such as a polyolefin or polymer blend such as polypropylene and polyethylene.

The porous, outer material may be formed of fabric, paper or non-dissolvable polymers or plastics, such as those commonly used to construct tea bags or tobacco snus pouches. In an embodiment, the porous, outer material may be flavored by coating the wrapper 14 with a flavorant containing coating. In an embodiment, the coating can include functional ingredients or salivation inducing ingredients. The pouch wrapper 14 can be colored to designate the inner filling material contained therein.

Figure 2:
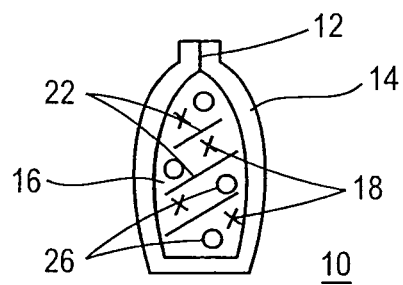
FIG. 2 is a cross-sectional view of the oral flavor delivery pouch product of FIG. 1.

In one embodiment, as seen in FIG. 2, the oral flavor delivery pouch product 10 includes a pouch wrapper 14 that contains an inner filling material 16. The inner filling material 16 may completely or partially fill the interior of the pouch wrapper 14. A seal 12 closes the edges of the pouch wrapper 14 to contain the inner filling material 16.

Preferably, the inner filling material 16 includes a non-tobacco, botanical component 18, at least one functional ingredient 26, and/or a solid flavor component 22, which can be in the form of a flavor strip. The inner filling material 16 can be loose or a solid mass. For example, the non-tobacco component 18 can be a mixture of granulated tea (e.g., 25 to 95 wt. %) and citrus fiber (e.g., 5 to 25 wt. %). For example, the filling can include 25 to 90 wt. % black tea and 8 to 25 wt. % citrus fiber (e.g., Citri-Fi 100 available from Fiberstar, Inc.). In an embodiment, the non-tobacco component can include citrus fiber in an amount of about 1% to about 99%.

The flavor strip may be formed of any polymer, wax, oil, tapioca, or other food grade material. Commercially available flavor strips (e.g. Listerine PocketPaks® manufactured by Warner-Lambert Company) may also be used. The flavor strip may include various flavors and may have microencapsulated flavorants and/or functional ingredients embedded therein.

In a preferred embodiment, the flavor strip is chopped and dispersed throughout the inner filling material 16. In an embodiment, the flavor strip can be ground, mixed with a binder, and formed into beads and/or bits that can be dispersed throughout the inner filling material 16. The films, beads and/or bits can include microcrystalline cellulose (MCC), food starch, carrageenan, sweeteners, and/or β-cyclodextrin. For example, the films, beads and/or bits can include tapioca or gelatin.

In an embodiment, the solid flavor component 26 can include additional flavor beads that can be prepared by mixing a flavorant and β-cyclodextrin in a solvent to prepare an encapsulated flavorant, drying the mixture to obtain a solid, and pulverizing the solid.

The flavor beads can have a diameter of about 0.1 mm to about 2.5 mm, preferably about 0.2 mm to about 1.2 mm, and more preferably about 0.3 mm to about 0.7 mm.

In a preferred embodiment, the inner filling material 16 includes about 1% to 50% solid flavor component 26 in the form of flavor beads, strips, and/or bits by weight based on the weight of the inner filling material. More preferably, the inner filling material 16 includes about 3% to about 40% solid flavor component 26 in the form of flavor beads, strips, and/or bits by weight based on the weight of the inner filling material.

Preferably, the non-tobacco, botanical component 18 of the inner filling material 16 is selected from botanical fibers, powders, beads, granules, capsules, microcapsules, gels, liquids, and/or semi-liquids including, but not limited to, tea fiber, tea extracts, coffees, coffee extracts, fruits, fruit extracts, spices, spice extracts, herbal-like ingredients, vegetable fibers, vegetable extracts and combinations thereof. In a preferred embodiment, the non-tobacco botanical component 18 may be disintegrable and/or dissolvable. Preferably, the pouch product 10 includes about 1% to about 95% of the non-tobacco botanical component by weight based on the weight of the pouch product.

In an embodiment, the inner filling material 16 can include beads, capsules and/or microcapsules that are designed to contain liquid, semi-liquid, and/or gel additives that are released when the beads, capsules, and/or microcapsules rupture due to mechanical action or pH change. In another embodiment, the beads, capsules and/or microcapsules can include powders and/or solids. In an embodiment, the user can control the release of the additives by choosing when to bite down on the beads, capsules, and/or microcapsules. The ingredients of the inner filling material can also be released by sucking, moisture, or other mechanisms.

In a preferred embodiment, the functional ingredient 26 contained in the inner filling material is a food grade functional ingredient. Preferably, the functional ingredient 26 is in the form of at least one functional capsule. Preferably, the capsules range in size from about 200 mesh to 20 mm in length. The capsules may include one or more various flavors, chemesthesis agents, vitamins, soothing agents, energizing agents, and the like. In one embodiment, the functional capsules provide an effervescent.

Also, the capsules may be made by various methods. For instance, the capsules may incorporate tapioca used for sequestering additional flavors and functional ingredients such as blueberry, cranberry, grape, honey, mint, or alcohol.

In another embodiment, the functional capsules can provide one or more soothing ingredients such as, without limitation, chamomile, lavender, jasmine, and the like. In another embodiment, the functional capsules also include at least one energizing ingredient or vitamin such as, without limitation, caffeine, taurine, guarana, vitamin B6, vitamin B12, and the like.

Also preferably, at least one capsule is included in the inner filling material 16. More preferably, between about 2 and 20 capsules are included in the inner filling material 16.

In one embodiment, multiple different functional ingredients 26 may be added. For example, one functional ingredient 26 may include an effervescent, while a second functional ingredient 26 includes a soothing ingredient.

In an embodiment, the inner filling material 16 can also include sweeteners. Preferred sweeteners include, without limitation, water soluble sweeteners such as monosaccharides, disaccharides, and polysaccharides. For example, sweeteners such as xylose, ribose, sucrose, maltose, fructose, glucose, sucralose, mannose, and sugar alcohols can be included.

Also preferably, the solid flavor component 22 of the inner filling material 16 includes flavorants. Exemplary flavorants include, but are not limited to, berry flavors such as pomegranate, acai, raspberry, blueberry, strawberry, boysenberry, and/or cranberry. Other suitable flavorants include, without limitation, any natural or synthetic flavor or aroma, such as menthol, peppermint, spearmint, wintergreen, bourbon, scotch, whiskey, cognac, hydrangea, lavender, chocolate, licorice, citrus and other fruit flavors, such as apple, peach, pear, cherry, plum, orange, lime, grape, and grapefruit, gamma octalactone, vanillin, ethyl vanillin, breath freshener flavors, butter, rum, coconut, almond, pecan, walnut, hazelnut, french vanilla, macadamia, sugar cane, maple, cassis, caramel, banana, malt, espresso, kahlua, white chocolate, spice flavors such as cinnamon, clove, cilantro, basil, oregano, garlic, mustard, nutmeg, rosemary, thyme, tarragon, dill, sage, anise, and fennel, methyl salicylate, linalool, jasmine, coffee, olive oil, sesame oil, sunflower oil, bergamot oil, geranium oil, lemon oil, ginger oil, balsamic vinegar, rice wine vinegar, and red wine vinegar. Preferred flavors include cinnamol, tymool, and/or tea tree.

Figure 3:
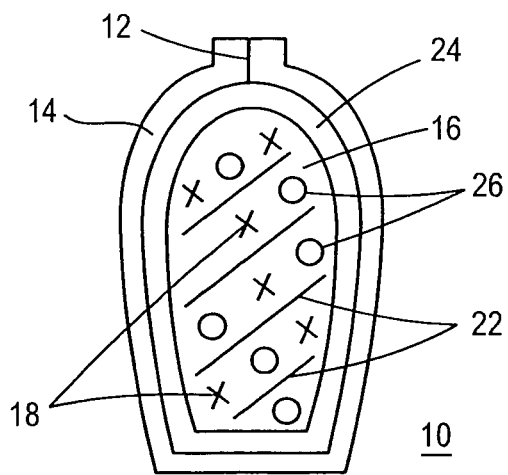
FIG. 3 is a cross-sectional view of a second embodiment of an oral flavor delivery pouch product.

In another preferred embodiment, as seen in FIG. 3, the oral flavor delivery system 10 can include a flavor strip liner 24. The flavor strip liner 24 may be made of the same materials as the flavor strip of the solid flavor component 22. Preferably, the flavor strip liner is interposed between the porous pouch wrapper 14 and the inner filling material 16. The inner flavor strip liner 24 can be about 0.03 mm to 1.0 mm thick.

Preferably, the flavor strip liner 24 and flavor beads each provide another flavor and/or texture to the oral flavor delivery system. The inner flavor strip liner 24 may be glycerin based, gelatin based, tapioca based, oil based, or wax based. Commercially available flavor strips are suitable for use as the flavor strip liner.

While the foregoing has been described in detail with reference to specific embodiments thereof, it will be apparent to one skilled in the art that various changes and modifications may be made, and equivalents thereof employed, without departing from the scope of the claims.

We claim:

1. A tobacco-free oral flavor delivery pouch product comprising:
   a porous pouch wrapper; and
   a tobacco-free inner filling material contained within said porous pouch wrapper comprising:
      a non-tobacco, botanical component;
      at least one capsule, wherein said at least one capsule includes (a) an effervescent; (b) a vitamin; (c) a soothing ingredient; (d) an energizing ingredient and/or (e) a chemesthesis agent and wherein the at least one capsule includes tapioca, the tapioca being operable to sequester flavors and/or functional ingredients;
      a solid flavor component comprising a first flavor strip; and
      a lining interposed between said porous pouch wrapper and said inner filling material, wherein said lining is made of a second flavor strip, the second flavor strip being tapioca based,
   wherein said at least one capsule and said solid flavor component are dispersed amongst said non-tobacco, botanical component,
   wherein said inner filling material is tobacco-free and the oral flavor delivery pouch delivers flavor upon placement in a user's mouth, and
   wherein the tobacco-free oral flavor delivery pouch delivers flavor for about 1 minute to about 60 minutes when placed in a user's oral cavity.

2. The tobacco-free oral flavor delivery pouch product of claim 1, wherein the thickness of said lining is about 0.03 mm to 1.0 mm.

3. The tobacco-free oral flavor delivery pouch product of claim 1, wherein said non-tobacco, botanical component is selected from the group consisting of fibers, teas, tea extracts, coffees, coffee extracts, fruits, fruit extracts, spices, spice extracts, herbal-like ingredients, and combinations thereof.

4. The tobacco-free oral flavor delivery pouch product of claim 1, wherein said at least one capsule is activated by mastication or sucking.

5. The tobacco-free oral flavor delivery pouch product of claim 1, wherein said first flavor strip comprises a polymer, a wax, an oil, and/or tapioca.

6. The tobacco-free oral flavor delivery pouch product of claim 1, wherein said at least one capsule includes a soothing ingredient that is selected from the group consisting of chamomile, lavender, jasmine, and combinations thereof.

7. The tobacco-free oral flavor delivery pouch product of claim 1, wherein said at least one capsule includes an energizing ingredient that is selected from the group consisting of caffeine, taurine, guarana, vitamin B6, vitamin B12, and combinations thereof.

8. The tobacco-free oral flavor delivery pouch product of claim 1, wherein said at least one capsule is about 1 mm to 20 mm in length.

9. The tobacco-free oral flavor delivery pouch product of claim 1, wherein said first flavor strip is chopped and dispersed amongst said inner filling material.

10. The tobacco-free oral flavor delivery pouch product of claim 1, wherein said solid flavor component is included in said inner filling material in an amount of about 1% to 50% by weight based on the weight of said inner filling material.

11. The tobacco-free oral flavor delivery pouch product of claim 1, wherein the weight of said inner filling material contained in said pouch is about 0.2 g to 2.0 g.

12. The tobacco-free oral flavor delivery pouch product of claim 1, wherein said porous pouch wrapper has a coating containing encapsulated flavorants, chemesthesis agents, vitamins, soothing agents, energizing agents and/or an effervescent.

13. The tobacco-free oral flavor delivery pouch product of claim 1, wherein said pouch product is formed in a crescent shape.

14. The tobacco-free oral flavor delivery pouch product of claim 1, wherein said pouch product is formed in a half moon, D-shape, oblong, cylindrical, tea leaf, tear drop, or hourglass shape.

15. The tobacco-free oral flavor delivery pouch product of claim 1, wherein said inner filling material includes about 2 to 10 capsules.

16. The tobacco-free oral flavor delivery pouch product of claim 1, wherein the pouch product is formed in a shape of a boomerang having a pair of arms, and wherein each of the arms extends around a gum line of a user.

17. The tobacco-free oral flavor delivery pouch product of claim 1, further comprising a flavor containing coating on an outer surface of the porous pouch wrapper.

18. A method of making the tobacco-free oral flavor delivery pouch product of claim 1 comprising:
   forming said porous pouch wrapper into an open pouch;
   filling said open pouch with said tobacco free inner filling material; and
   sealing said open pouch.

19. The method of claim 18, wherein the wrapper is a polymer material and the inner filling material includes 25 to 90 wt. % black tea powder and 8 to 25 wt. % citrus fiber powder.

* * * * *